US00PP18066P3

(12) United States Plant Patent
Larsen

(10) Patent No.: US PP18,066 P3
(45) Date of Patent: Sep. 25, 2007

(54) *OSTEOSPERMUM* PLANT NAMED 'SHIELA'

(50) Latin Name: *Osteospermum ecklonis (DC) T. Norl.*
Varietal Denomination: Shiela

(75) Inventor: Bjarne Nyholm Larsen, Odense N (DK)

(73) Assignee: Sunny Gronnegyden APS, Odense N (DK)

( * ) Notice: Subject to any disclaimer, the term of this patent is extended or adjusted under 35 U.S.C. 154(b) by 43 days.

(21) Appl. No.: 11/184,071

(22) Filed: Jul. 19, 2005

(65) Prior Publication Data

US 2007/0022506 P1 Jan. 25, 2007

(30) Foreign Application Priority Data

Jul. 19, 2004 (EM) ..... 2004/1398

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Foley & Lardner LLP

(57) ABSTRACT

A new distinct cultivar of *Osteospermum* plant named 'Shiela', characterized by short, dense and bushy plant form with inverse pyramidal shape; more upright stems and differently shaped leaves; more large, upright inflorescences per plant consisting of ray florets that are primarily orange-red in color with red-purple color at base, and dark red-purple disc florets; and vigorous growth habit.

3 Drawing Sheets

Figure 1:
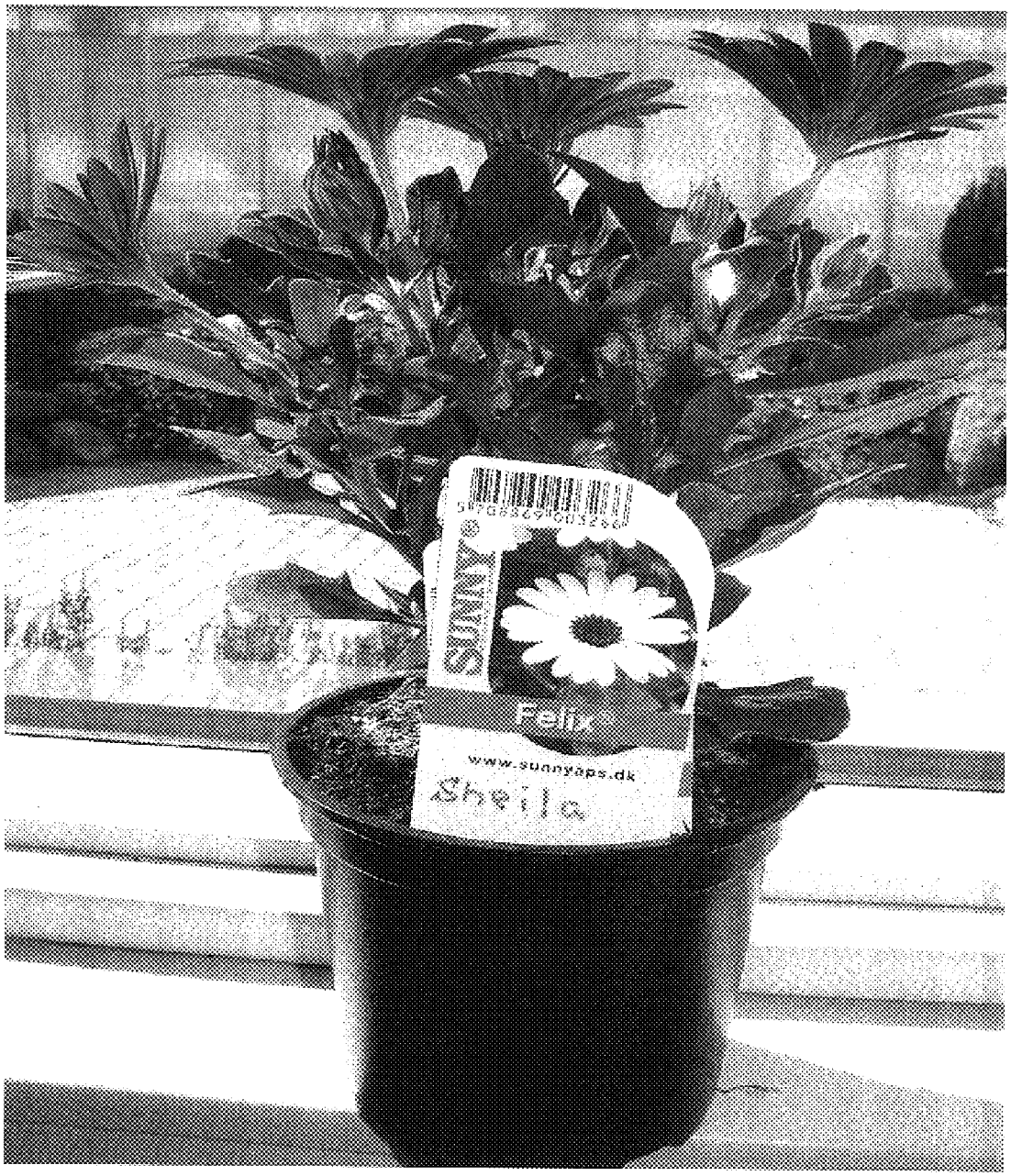

Botanical designation: *Osteospermum ecklonis* (*DC*) *T. Norl.*
Cultivar denomination: 'Shiela'.

BACKGROUND OF THE INVENTION

The present Invention relates to a new and distinct cultivar of *Osteospermum* plant, botanically known as *Osteospermum ecklonis* (*DC*) *T. Norl.*, commonly known as Cape Daisy and hereinafter referred to by the cultivar denomination 'Shiela'.

The new *Osteospermum* is a product of a planned breeding program conducted by the Inventor, Bjarne Larsen, in Stige, Odense, Denmark. The objective of the breeding program is to develop a new *Osteospermum* cultivar with upright, compact plant habit, interesting inflorescence color, good branching performance, low growth retardant requirements and low temperature tolerance.

The new *Osteospermum* originated from a planned crossing made by the Inventor in 2003 in Stige, Odense, Denmark. The female or seed parent is 'Sunny Serena', (patented, U.S. Plant Pat. No. 15,693). The male or pollen parent is *Osteospermum ecklonis* cultivar designated '30.013.01' (unpatented). The new *Osteospermum* cultivar 'Shiela' was selected by the Inventor as a flowering plant within the progeny of the above crossing in 2003 in a controlled environment in Stige, Odense, Denmark.

Asexual reproduction of the new *Osteospermum* cultivar by apical stem cuttings was first performed in June of 2003 in Stige, Odense, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be unique characteristics of 'Shiela'. These characteristics in combination distinguish 'Shiela' as a new and distinct cultivar:

1. short, dense and bushy plant form with inverse pyramidal shape;
2. more upright stems and differently shaped leaves;
3. more large, upright inflorescences per plant consisting of ray florets that are primarily orange-red in color with red-purple color at base, and dark red-purple disc florets; and
4. vigorous growth habit.

Plants of the new cultivar 'Shiela' differ from plants of the parental cultivar, 'Sunny Serena' (patented, U.S. Plant Pat. No. 15,693) in the characteristics described in Table 1.

TABLE 1

| Trait | New Cultivar 'Shiela' | Female Parent 'Sunny Serena' (patented) |
|---|---|---|
| Plant Height | About 16 cm | About 17 cm |
| Plant Diameter | About 18 | About 17 cm |
| Overall Plant Shape | Inverse Pyramidial | Globular |
| Number of Lateral Branches | 5 primary, 13 secondary (flowering) | 4 primary, 7 secondary |
| Lateral Branch Length | Primary: 3–5 cm, Secondary: 4–8 cm | Primary: About 3 cm, Secondary: 7–12 cm |
| Quantity of Leaves per Lateral Branch | 15–18 | 10–15 |
| Internode Length | 4–12 mm | About 3 mm |
| Number of | Freely flowering, | Freely flowering, about |

TABLE 1-continued

| Trait | New Cultivar 'Shiela' | Female Parent 'Sunny Serena' (patented) |
|---|---|---|
| Inflorescences per Plant | more than 30 buds and open inflorescences. | 13 to 30 buds and open inflorescences. |
| Inflorescence Diameter | 7–8 cm | 6–7 cm |
| Ray Floret Color (fully opened) | Towards Apex, RHS 30A Towards Base, RHS N74B With Stripes of RHS N34B | Towards Apex, RHS 10A Towards Base, RHS 158D |
| Disc Floret Color (when opening) | Primarily RHS 59A Towards Apex, RHS 183A, and periphery RHS 22C | Greyed-white, RHS 156A |
| Peduncle Length | About 10 cm | 5–7 cm |
| Anther Color | Black, RHS 202A | Dark Blue, RHS N99B |

Plants of the parental cultivar, '30.013.01' (unpatented) were unavailable to provide a comparison description to plants of the new cultivar 'Shiela'.

Of the many commercial cultivars known to the present Inventor, the most similar in comparison to the new *Osteospermum* cultivar 'Sunny Shiela' is the parental cultivar 'Sunny Serena' as described in Table 1.

BRIEF DESCRIPTION OF THE PHOTOGRAPHS

The accompanying colored photographs illustrate the overall appearance of the new *Osteospermum* cultivar 'Shiela' showing the colors as true as is reasonably possible with colored reproductions of this type. Colors in the photographs may differ slightly from the color values cited in the detailed botanical description which accurately describe the color of the new *Osteospermum* cultivar 'Shiela'.

1. FIG. 1 shows a side perspective view of a typical potted flowering plant of 'Shiela', as a produced cultivar 20 weeks after planting.

Figure 2:
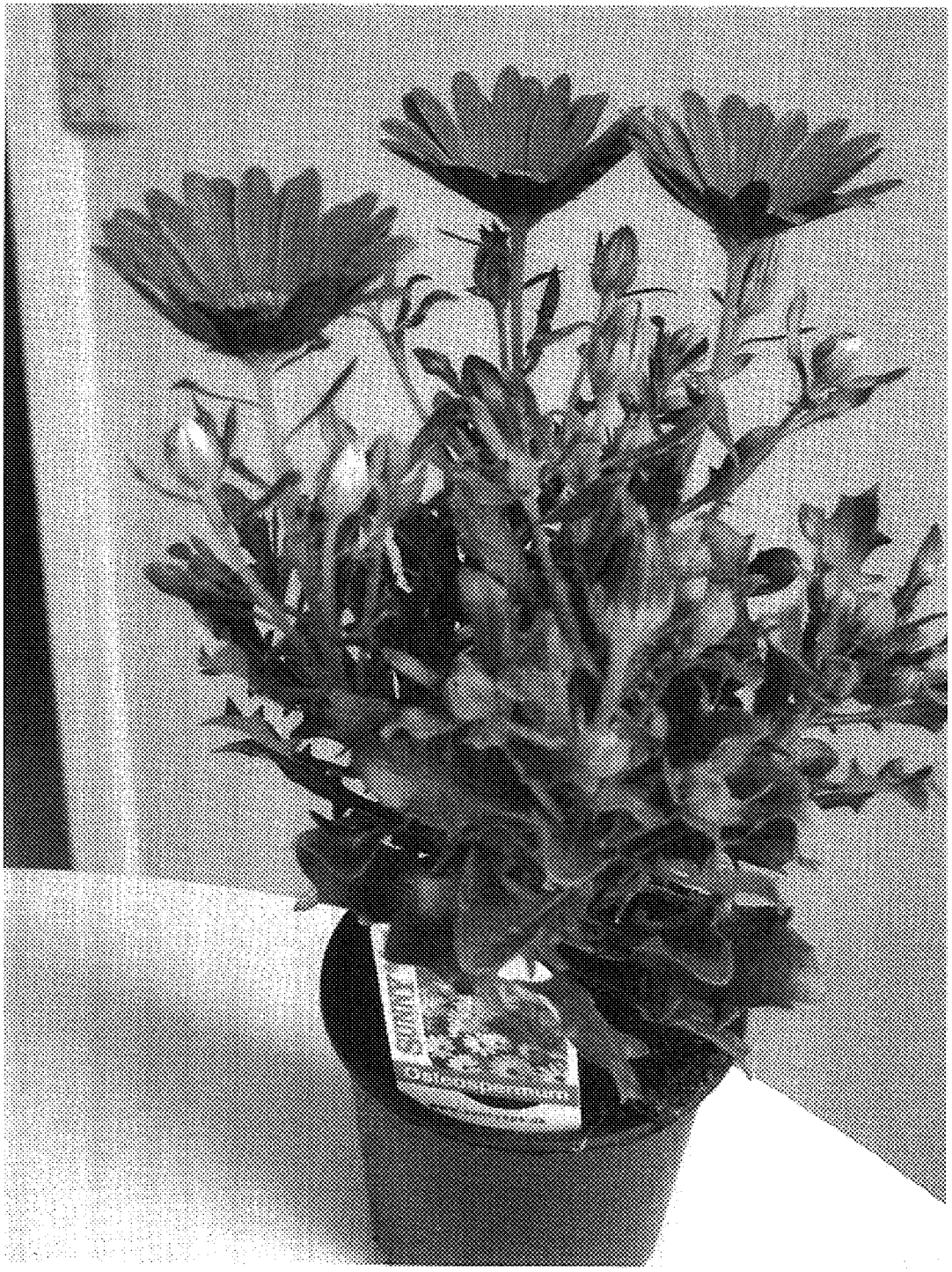

2. FIG. 2 shows a close-up side perspective view of a typical potted flowering plant of 'Shiela', as a produced cultivar 20 weeks after planting.

Figure 3:
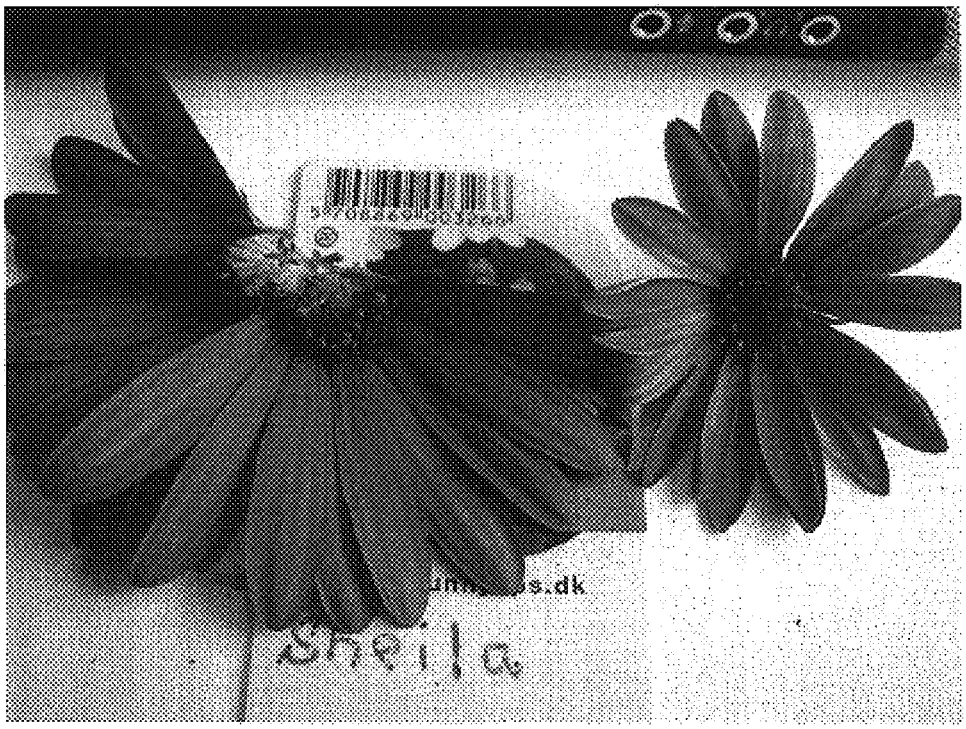

3. FIG. 3 shows a top perspective view of inflorescences of 'Shiela' (photograph on top half), as a produced cultivar 20 weeks after planting.

Figure 4:
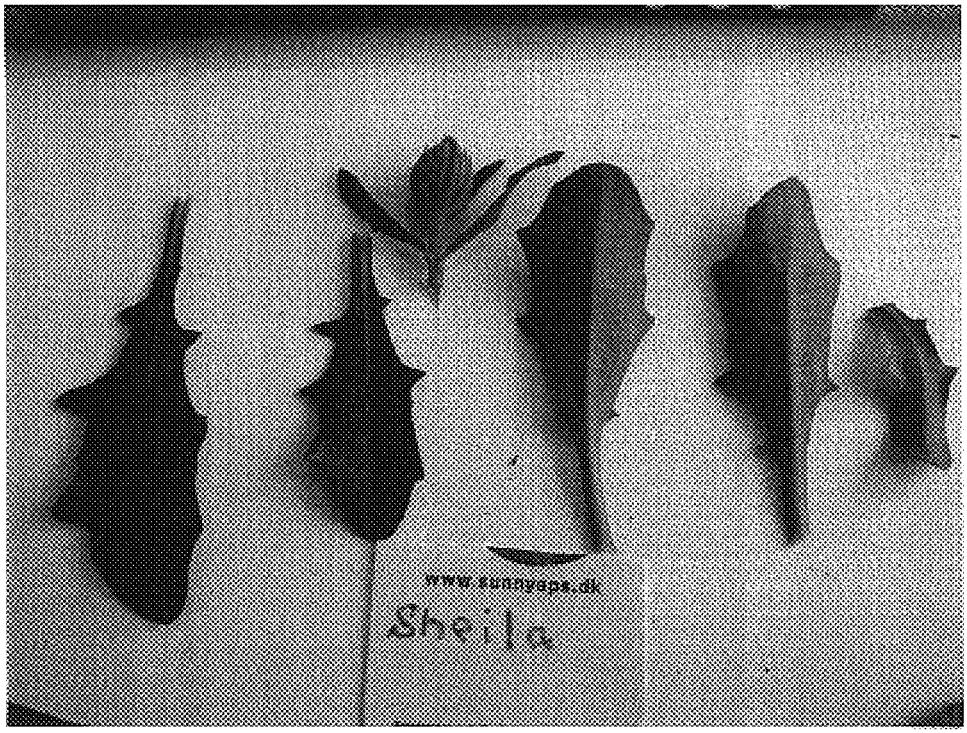

4. FIG. 4 shows a top and bottom view of leaves and a bud of 'Shiela', as a produced cultivar 20 weeks after planting.

DETAILED BOTANICAL DESCRIPTION

The new *Osteospermum* cultivar 'Shiela' has not been observed under all possible environmental conditions. The phenotype of the new cultivar may vary with variations in environment such as temperature, light intensity, and day length, without any change in the genotype of the plant.

The aforementioned photographs, together with the following observations, measurements and values describe plants of the new *Osteospermum* cultivar 'Shiela' as grown in a greenhouse and outside in Stige, Odense, Denmark, under conditions which closely approximate those generally used in commercial practice and garden use. Vegetative propagation with apical tip cuttings (4–5 leaves) took place in a greenhouse with propagation tents for 3 weeks with the day and night temperature averaging about 20° C. The temperature was then lowered to the day and night temperature averaging about 14° C. The plants were subirrigated with a nutrient solution of 2–3 mS when needed and given supplementary irradiation with SON T lamps having an installed energy level of 400 $Wm^2$.

Color references are made of The Royal Horticultural Society Colour Chart (R.H.S.), $4^{th}$ edition 2000, except where general colors of ordinary significance are used. The photographs and descriptions were taken during the spring season when outdoor day temperatures ranged from 7° C. to 15° C. and outdoor night temperatures ranged from 0° C. to 7° C. The age of the plants described is 20 weeks after planting.

Botanical classification: *Osteospermum ecklonis* (*DC*) *T. Norl.*

Parentage:

*Female or seed parent.*—*Osteospermum ecklonis* (*DC*) *T. Norl.* 'Sunny Serena' (patented, U.S. Plant Pat. No. 15,693).

*Male or pollen parent.*—*Osteospermum ecklonis* (*DC*) *T. Norl.* designated '30.013.01' (unpatented).

Propagation:

*Type.*—Apical stem cutting.

*Time and temperature to initiate roots.*—Summer: About 12 to 14 days at 20° C. to 22° C. in tunnels in a greenhouse. Winter: About 17 to 20 days at 20° C. to 22° C. in tunnels in a greenhouse.

*Time and temperature to develop roots.*—Summer: About 14 to 18 days at 20° C. to 22° C. in tunnels in a greenhouse. Winter: About 20 to 22 days at 20° C. to 22° C. in tunnels in a greenhouse.

*Rooting description.*—100% rooting.

*Rooting habit.*—Fine, fibrous and branching.

Plant description:

*General appearance and form.*—Perennial plant used as a bedding or potted plant with inflorescences in composite heads.

*Growth and branching habit.*—Freely branching with lateral flowering branches forming at every node; dense and bushy.

*Growth rate/vigor.*—Vigorous.

*Plant height* (soil level to top of plant plane).—About 16 cm.

*Plant width* (*spread*).—About 18 cm.

*Plant strength.*—Withstands temperature down to +1° C. and up to +35° C., but at +35° C. flowering may cease.

*Crop time to produce a mature flowering plant.*—After rooting, about 16 weeks are required to produce finished flowering plants in 11 cm pots.

Branches:

*Number of branches per plant.*—5 primary, 13 secondary.

*Length.*—Primary: About 3–5 cm. Secondary: 4–8 cm (including flower).

*Diameter.*—About 4–5 mm.

*Internode length.*—About 4–12 mm.

*Strength.*—Strong.

*Aspect.*—Upright.

*Texture.*—Glabrous.

*Color.*—Yellow-green, RHS 144C.

Foliage description:

*Arrangement.*—Alternate (5-whorl), entire, lobed ovate to spatulate.

*Leaf length.*—About 3–8 cm.

*Leaf width.*—About 1–3 cm.

*Overall shape of leaf.*—Ovate to spatule, prominent lobes.

*Shape at apex.*—Mature leaf: obtuse. Young leaf: acute.

*Shape at base.*—Attenuate, decurrent.

*Margin.*—Entire, 4 triangular lobes.

*Texture.*—Upper and lower surface: scattered short stiff hairs.

*Color of developing foliage.*—Upper surface: Yellow-green, RHS 147A. Lower surface: Yellow-green, RHS 148C.

*Color of mature foliage.*—Upper surface: Green, RHS 139A. Lower surface: Yellow-green, RHS 147A.

*Venation pattern.*—Brochidodromus, form of pinnate.

*Petiole length.*—About 1–2 cm.

*Petiole diameter.*—About 2–4 mm.

*Petiole texture.*—Upper surface: glabrous. Lower surface: glabrous with scattered short stiff hairs.

*Petiole color.*—Upper surface: Yellow-green, RHS 145B. Lower surface: Yellow-green, RHS 145C.

Inflorescence description:

*Appearance.*—Terminal and axillary inflorescences held above and beyond the foliage. Composite daisy inflorescence form, radially symmetrical, with ligulate-shaped ray florets and disc florets massed at the center; ray and disc florets arranged acropetally on a capitulum. Inflorescences face upright.

*Natural flowering season.*—Continuous throughout the spring and summer in temperate regions. Season can be extended by vernalization and long day treatments. Flowering may cease if night temperatures exceed +25° C. for several weeks.

*Time to flower.*—7 to 14 days (longevity of individual inflorescences is dependent on temperature and light conditions).

*Postproduction longevity.*—Inflorescences maintain good color and substance for about 14 days on the plant when grown in an outdoor environment. Inflorescences persistent, but wither to almost insignificance.

*Quantity of inflorescences.*—Freely flowering; more than 30 open inflorescences and inflorescence buds per plant.

*Fragrance.*—Weak lemon scent.

*Bud.*—Rate of opening (from showing color to fully open inflorescence): 4 to 6 days. Length: About 2 cm. Diameter: About 1 cm. Shape: Globular to ovoid. Color: Yellow-green, RHS 146C (base) to yellow-green, RHS 145B (apex).

*Peduncle.*—Length: Terminal: About 10 cm. Secondary: About 7 cm. Tertitary: About 5 cm. Diameter: About 2 mm. Appearance and angle: Terminal: About 5 to 10 degrees from vertical. Secondary: About 30 to 45 degrees from vertical. Tertiary: About 30 to 45 degrees from vertical) Strength: Strong. Texture: Glabrous. Color: Yellow-green, RHS 144C.

*Inflorescence.*—Inflorescence depth (height): About 6 mm. Inflorescence diameter About 7.5 cm. Receptacle diameter: About 17 mm. Receptacle height: About 14 mm. Receptacle shape: Conical (inverted). Receptacle color: Yellow-green, RHS 145D.

*Ray florets.*—Quantity per inflorescence: Typical number: 20 in 1½ whorl. Observed number: 18–22. Length: Range: 32–38. Observed: About 35 mm. Width: About 8–10 mm. Overall shape: Oblanceolate. Shape at apex: Acute with very slight retuse. Shape at base: Cuneate. Margin: Entire. Texture: Upper surface: velvety. Lower surface: shiny. Orientation: Initially 45 degrees from vertical, with development, to 30 degrees from vertical. Ray Floret Color (when opening): Upper surface: RHS 34C, orange-red tip to RHS 67A, red-purple base, longitudinal stripes of RHS 25A, orange. Lower surface: RHS 178A, grayed red, stripes of RHS 185B, grayed purple, few spots and edges RHS 163B grayed orange Ray Floret Color (when fully opened): Upper surface: RHS 30A, orange-red tip to RHS N74B base, red-purple, stripes of RHS N34B, dark orange-red. Lower surface: Stripes of gray-orange RHS 176A.

*Disc florets.*—Quantity per inflorescence: Typical number: 70. Observed number: 60–80. Length: About 6 mm. Width: At apex: About 2–3 mm. At base: About 1–2 mm. Disc area diameter: About 15 mm. Overall shape: Tubular. Shape at apex: Star with 5 triangular tips. Shape at base: Fused to tube. Margin: Entire. Texture: Upper surface: glabrous. Lower surface: glabrous. Disc Florets Color (when opening): Upper surface: Primarily RHS 59A, dark red-purple, with apex RHS 183A, and periphery RHS 22C yellow-orange. Lower surface: White, RHS N155D. Disc Florets Color (when fully opened): Upper surface: Primarily RHS 59A, dark red-purple, and periphery RHS 22C, yellow-orange. Lower surface: White, RHS N155D.

*Phyllaries.*—None.

Reproductive organs:

*Androecium* (*on disc florets only*).—Stamen number: 5 per floret; fused around style. Stamen length: About 2 mm. Anther shape: Linear. Anther length: About 1 mm. Anther color: Black, RHS 202A. Pollen amount: Plenty. Pollen color: Orange, RHS N25A.

*Gynoecium* (*on ray and disc florets*).—Quantity: 1 per floret. Pistil length: About 4 mm. Stigma shape: Brush. Stigma color: Purple, RHS N187. Style length: About 2 mm. Style color: White, RHS 155B. Ovary color: Green-yellow, RHS 2D.

Seed: None observed at this stage of development.

Fruit: None observed.

Disease/pest resistance: Good.

Disease/pest susceptibility: Low.

Temperature tolerance: Plants of the new *Osteospermum* have exhibited good tolerance to draught, rain and wind, however flowering may cease during hot periods (night temperatures above 25° C.). Low temperature tolerance to 1° C.

Growth retardant(s): 3 times 0.2% Chlormequat drench during production.

I claim:

1. A new and distinct cultivar of *Osteospermum* plant named 'Shiela', as illustrated and described herein.

* * * * *